United States Patent
Schwindt (10) Patent No.: US 11,928,970 B2
(45) Date of Patent: Mar. 12, 2024

(54) AIRCRAFT AND METHOD OF ADJUSTING A PILOT WORKLOAD

(71) Applicant: GE Aviation Systems Limited, Cheltenham (GB)

(72) Inventor: Stefan Alexander Schwindt, Cheltenham (GB)

(73) Assignee: GE Aviation Systems Limited, Cheltenham (GB)

( * ) Notice: Subject to any disclaimer, the term of this patent is extended or adjusted under 35 U.S.C. 154(b) by 778 days.

(21) Appl. No.: 16/709,409

(22) Filed: Dec. 10, 2019

(65) Prior Publication Data

US 2020/0184833 A1 Jun. 11, 2020

(30) Foreign Application Priority Data

Dec. 11, 2018 (GB) ...................................... 1820118

(51) Int. Cl.
*G08G 5/00* (2006.01)
*A61B 5/16* (2006.01)
*A61B 5/18* (2006.01)
*G06Q 10/0631* (2023.01)

(52) U.S. Cl.
CPC ........... *G08G 5/0039* (2013.01); *A61B 5/165* (2013.01); *A61B 5/18* (2013.01); *G06Q 10/06311* (2013.01)

(58) Field of Classification Search
CPC ........ G08G 5/0039; A61B 5/165; A61B 5/18; G06Q 10/06311
USPC ........................................................ 340/945
See application file for complete search history.

(56) References Cited

U.S. PATENT DOCUMENTS

| | | |
|---|---|---|
| 5,243,339 A | 9/1993 | Graham et al. |
| 5,900,827 A | 5/1999 | Graham et al. |
| 6,070,098 A | 5/2000 | Moore-Ede et al. |
| 7,301,464 B2 | 11/2007 | Coulter |
| 7,437,225 B1 | 10/2008 | Rathinam |
| 8,164,464 B2 | 4/2012 | Matos |
| 8,200,379 B2 | 6/2012 | Manfredi et al. |

(Continued)

FOREIGN PATENT DOCUMENTS

| | | |
|---|---|---|
| EP | 3196725 A1 | 7/2017 |
| EP | 3249587 A1 | 11/2017 |

(Continued)

OTHER PUBLICATIONS

European Patent Office, Extended Search Report re Corresponding Application No. 19214150.5-1203, dated May 7, 2020, 9 pages, Munich, Germany.

*Primary Examiner* — Zhen Y Wu
(74) *Attorney, Agent, or Firm* — McGarry Bair PC (57) ABSTRACT

A method of adjusting an operator workload during a travel segment including tracking over a time period, using at least one sensor, one of inputs by an operator indicative of an operator workload or image sensor data or a biometric parameter indicative of an operator stress level during the travel segment. Determining, using a controller that is operatively connected to the at least one sensor, a level of one of the operator workload or operator stress level. The method also includes adjusting, using a controller that is operatively connected to the control computer, the operator workload when the level of one of the operator workload or operator stress level exceeds a predetermined threshold.

10 Claims, 5 Drawing Sheets

(56) References Cited

U.S. PATENT DOCUMENTS

| | | | |
|---|---|---|---|
| 8,514,104 B1* | 8/2013 | Dirks | G08G 5/0021 340/945 |
| 8,552,850 B2 | 10/2013 | De Mers et al. | |
| 8,766,819 B2 | 7/2014 | Dorfmann et al. | |
| 8,928,498 B2 | 1/2015 | Dorneich et al. | |
| 8,972,106 B2 | 3/2015 | Prakah-Asante et al. | |
| 9,037,410 B2* | 5/2015 | Ferro | G08G 5/0039 701/14 |
| 9,227,736 B2 | 1/2016 | Whitlow et al. | |
| 9,446,852 B2 | 9/2016 | Lacko et al. | |
| 9,613,543 B2 | 4/2017 | Whitlow et al. | |
| 9,637,133 B1 | 5/2017 | McCusker et al. | |
| 9,701,418 B2 | 7/2017 | Nelson et al. | |
| 9,786,189 B2 | 10/2017 | Loussides et al. | |
| 9,905,108 B2 | 2/2018 | Kaplan et al. | |
| 9,919,712 B1 | 3/2018 | Doyen et al. | |
| 10,556,703 B1* | 2/2020 | Skola | G08G 5/0065 |
| 2003/0074092 A1* | 4/2003 | Carrabis | G16H 10/20 700/90 |
| 2004/0239550 A1* | 12/2004 | Daly, Jr. | G01S 13/953 342/26 B |
| 2007/0182529 A1* | 8/2007 | Dobler | B60W 40/08 340/438 |
| 2008/0071434 A1* | 3/2008 | Fortier | G08G 5/0034 701/15 |
| 2009/0105943 A1* | 4/2009 | Ferro | G08G 5/0039 701/533 |
| 2010/0004803 A1 | 1/2010 | Manfredi et al. | |
| 2010/0106346 A1* | 4/2010 | Badli | G01C 23/00 701/3 |
| 2010/0134302 A1 | 6/2010 | Ahn et al. | |
| 2011/0102570 A1* | 5/2011 | Wilf | G06F 3/017 345/156 |
| 2011/0118908 A1* | 5/2011 | Boorman | G08G 5/0021 701/14 |
| 2012/0075119 A1* | 3/2012 | Dorneich | G06Q 10/06 340/945 |
| 2012/0075123 A1* | 3/2012 | Keinrath | G08G 5/0021 340/963 |
| 2012/0116186 A1 | 5/2012 | Shrivastav et al. | |
| 2012/0256749 A1* | 10/2012 | Rao | A61B 5/0022 701/1 |
| 2012/0319869 A1* | 12/2012 | Dorfmann | G08B 21/06 340/945 |
| 2013/0070043 A1* | 3/2013 | Geva | A61B 5/18 348/14.02 |
| 2014/0039757 A1* | 2/2014 | Prakah-Asante | A61B 5/1118 701/36 |
| 2014/0253722 A1* | 9/2014 | Smyth | B60W 40/072 348/135 |
| 2014/0343765 A1* | 11/2014 | Suiter | G08G 5/0091 701/18 |
| 2015/0302653 A1* | 10/2015 | Algreatly | G06F 3/041 345/633 |
| 2016/0093217 A1* | 3/2016 | Hale | G08G 5/0091 701/120 |
| 2016/0093221 A1* | 3/2016 | Bailey | G08G 5/0013 701/120 |
| 2016/0299506 A1* | 10/2016 | Bruggeman | G05D 1/106 |
| 2017/0115124 A1* | 4/2017 | Mullen | G01C 21/3697 |
| 2017/0213467 A1* | 7/2017 | Loussides | G08G 5/02 |
| 2017/0334456 A1* | 11/2017 | Deligianni | B60W 50/14 |
| 2017/0336789 A1* | 11/2017 | Sane | G06Q 10/0631 |
| 2018/0032300 A1* | 2/2018 | Singh | B60K 35/00 |
| 2019/0090800 A1* | 3/2019 | Bosworth | A61B 5/0015 |
| 2019/0232966 A1* | 8/2019 | Prakah-Asante | G06V 20/597 |
| 2019/0283778 A1* | 9/2019 | Dias | G02B 27/0179 |
| 2019/0340935 A1* | 11/2019 | Bhuyar | G08G 5/0021 |

FOREIGN PATENT DOCUMENTS

| | | |
|---|---|---|
| EP | 3415416 A1 | 12/2018 |
| KR | 101663922 B1 | 10/2016 |

* cited by examiner

AIRCRAFT AND METHOD OF ADJUSTING A PILOT WORKLOAD

BACKGROUND

This application claims priority to and benefit of GB Patent Application No. 1820118.6 filed Dec. 11, 2018, which is incorporated herein in its entirety.

BACKGROUND

Contemporary aircraft travel flight paths that generally includes a climb, a cruise, and a descent. Pilots along with flight management systems (FMS) implement the flight plan. The FMS may generate the flight plan by taking into account parameters specific to the aircraft and to the flight conditions such as the payload, the weight of the aircraft, the quantity of fuel onboard, temperature, wind, altitude, etc., and of the time constraints imposed by the air traffic control. The flight plan may describe all the waypoints or positions through which the aircraft is to pass, with the altitude and corresponding speed at each waypoint.

BRIEF DESCRIPTION

In one aspect, the disclosure relates to a method of adjusting pilot workload during a flight includes tracking over a time period, using at least one sensor, one of inputs by a pilot indicative of a pilot workload or image sensor data or a biometric parameter indicative of a pilot stress level during flight of the aircraft. Determining, using a controller that is operatively connected to the at least one sensor, a level of one of the pilot workload or pilot stress level. The method also includes adjusting, using a controller that is operatively connected to the flight control computer, the pilot workload when the level of one of the pilot workload or pilot stress level exceeds a predetermined threshold.

In another aspect, the disclosure relates to a method of adjusting a planned pilot workload before the planned flight. The method includes tracking over a time period, using at least one sensor, inputs by a pilot indicative of a pilot workload or image sensor data or a biometric parameter indicative of a pilot stress level during one or more flights of an aircraft prior to the assigned flight. Correlating, using a controller that is operatively connected to the at least one sensor, one of the image sensor data, biometric parameters or pilot workload with one or more time periods for analysis. Identifying, using a processor that is operatively connected to a controller, which of the one or more time periods comprise pilot workload above a threshold value based on the analysis. Adjusting, a controller that is operatively connected to the flight control computer, the pilot workload during the time periods above the threshold value of pre-planned pilot workload of the assigned flight.

DETAILED DESCRIPTION

Aspects of the present disclosure are directed to a method of adjusting a pilot workload during a flight. As used herein, workload means the tasks a pilot must perform during various stages of the flight. During operation of an aircraft, portions of a flight plan such as takeoff, landing or even flying over certain geographic areas can require significant pilot attention and workload and in some cases can increase a pilot's stress level. Other portions of a flight plan, such as cruise during long flights, may need minimal pilot attention. It can be beneficial to track a pilot's workload or stress level during flight and adjust the pilot's workload when the pilot's stress level or workload exceeds a predetermined threshold.

The present disclosure is also directed to a method of adjusting a pre-planned workload before a fight. Since flights often take place over the same flight path, such as from city-to-city, flight data can be collected that is representative of a typical flight. During any given flight, data representing a pilot's workload or stress level can be collected and correlated with portions of a flight plan such as takeoff, landing or flying over certain geographic areas. Statistical analysis of the data can determine when a pilot has experienced high workload volumes or high stress levels. The data can be saved and analyzed to understand when a pilot will likely experience increases in workload for a similar future planned flight. Prior to a future flight, it can be beneficial to understand when a pilot will likely experience higher workloads during the flight. In this scenario, it may be possible to adjust the expected pilot work load during heavy workload periods by shifting tasks during the heavy workload period to light workload periods. Moreover, understanding workloads during a flight can help airlines adjust crew rosters to adjust for workload conditions.

For purposes of illustration, the present disclosure will be described in the context of a flight management system in an aircraft environment. It will be understood, however, that the disclosure is not so limited and may have general applicability in non-aircraft applications, such as other mobile applications.

As used herein, "a set" can include any number of the respectively described elements, including only one element. All directional references (e.g., radial, axial, proximal, distal, upper, lower, upward, downward, left, right, lateral, front, back, top, bottom, above, below, vertical, horizontal, clockwise, counterclockwise, upstream, downstream, forward, aft, etc.) are only used for identification purposes to aid the reader's understanding of the present disclosure, and do not create limitations, particularly as to the position, orientation, or use of the disclosure. Connection references (e.g., attached, coupled, connected, and joined) are to be construed broadly and can include intermediate members between a collection of elements and relative movement between elements unless otherwise indicated. As such, connection references do not necessarily infer that two elements are directly connected and in fixed relation to one another. The exemplary drawings are for purposes of illustration only and the dimensions, positions, order, and relative sizes reflected in the drawings attached hereto can vary.

As used herein, a "controller" can include at least one processor and memory. Non-limiting examples of the memory can include Random Access Memory (RAM), Read-Only Memory (ROM), flash memory, or one or more different types of portable electronic memory, such as discs, DVDs, CD-ROMs, etc., or any suitable combination of these types of memory. The processor can be configured to run any suitable programs or executable instructions designed to carry out various methods, functionality, processing tasks, calculations, or the like, to enable or achieve the technical operations or operations described herein. The program can include a computer program product that can include machine-readable media for carrying or having machine-executable instructions or data structures stored thereon. Such machine-readable media can be any available media, which can be accessed by a general purpose or special purpose computer or other machine with a processor. Generally, such a computer program can include routines, programs, objects, components, data structures, algorithms, etc., that have the technical effect of performing particular tasks or implement particular abstract data types.

Figure 1:
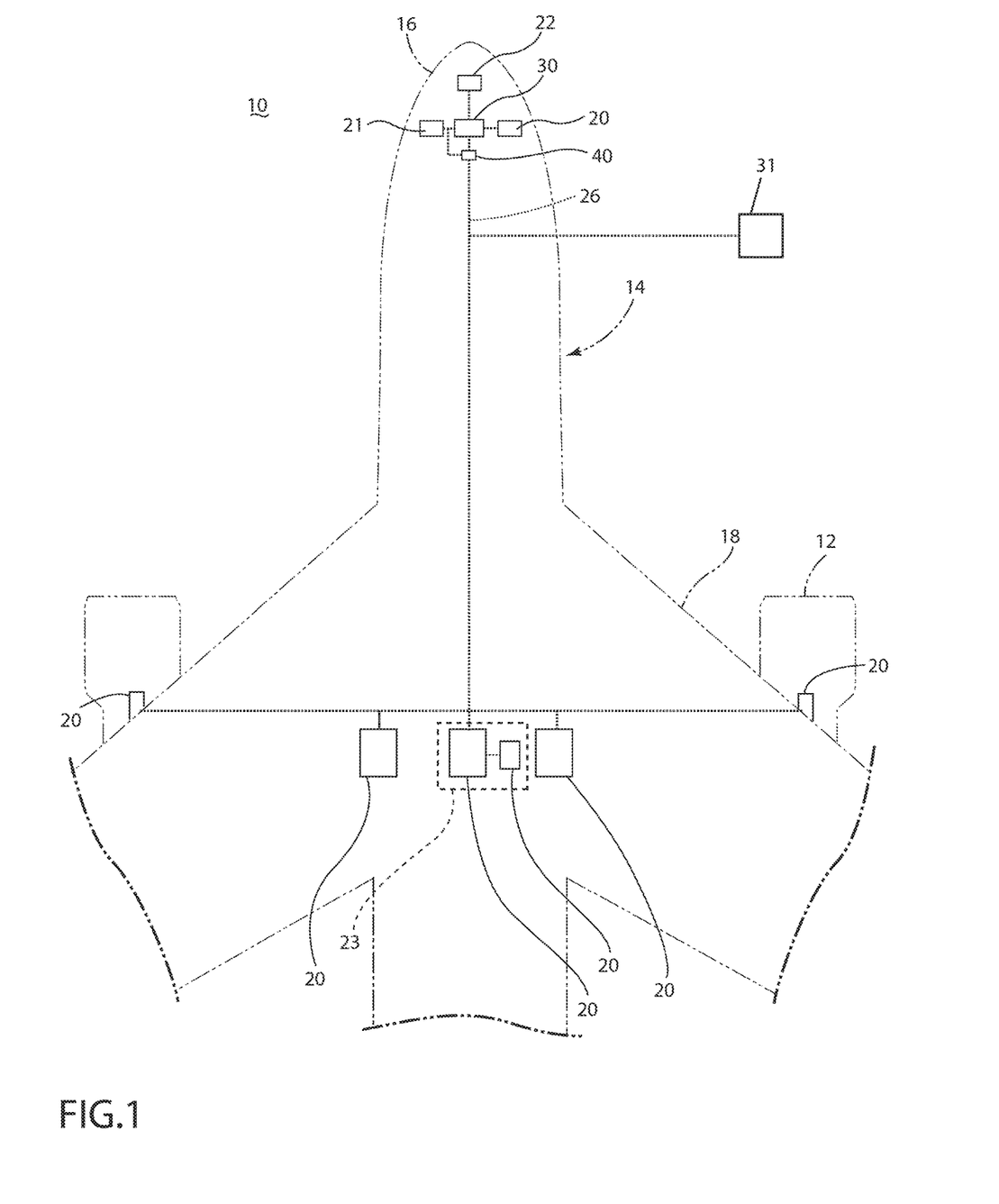
FIG. 1 is a top-down schematic view of a portion of an aircraft according to various aspects described herein.

FIG. 1 schematically illustrates an aircraft 10 according to various aspects described herein. One or more propulsion engines 12 can be coupled to a fuselage 14, a cockpit 16 can be positioned in the fuselage 14, and wing assemblies 18 can extend outward from the fuselage 14. A plurality of aircraft systems 20 that enable proper operation of the aircraft 10 can be included as well as a flight control computer 22 (or "computer" 22). While a commercial aircraft has been illustrated, it is contemplated that aspects of the disclosure can be used in any type of legacy aircraft, for example, without limitation, fixed-wing, rotating-wing, rocket, or personal aircraft.

The plurality of aircraft systems 20 can reside within the cockpit 16, within an electronics and equipment bay 23, or in other locations throughout the aircraft 10 including that they can be associated with the engines 12. Such aircraft systems 20 can include but are not limited to: an electrical system, an oxygen system, hydraulics and/or pneumatics system, a fuel system, a propulsion system, navigation systems, flight controls, audio/video systems, an Integrated Vehicle Health Management (IVHM) system, and systems associated with the mechanical structure of the aircraft 10. A variety of aircraft systems 20 have been illustrated for exemplary purposes and it will be understood that they are only a few of the systems that can be included in the aircraft 10.

A data network 26 over which the plurality of aircraft systems 20 can communicate with each other and provide information to a crew of the aircraft 10 can be included. For example, the aircraft systems 20 can output various information to a flight deck 30 located in a cockpit 16 of the aircraft 10.

A communication interface 40 can be located within the aircraft 10 and operably coupled to at least some of the plurality of aircraft systems 20. The communication interface 40 has been illustrated as being included in the cockpit 16. It is contemplated that the communication interface 40 can be located in other locations within the aircraft 10 including within the electronics and equipment bay 23. Although only one communication interface 40 has been illustrated, it is contemplated that the aircraft 10 can have multiple communication interfaces. The communication interface 40 can be utilized for communication with other aircraft or a ground station 31, such as by radio contact in a non-limiting example. In addition, the communication interface 40 can transmit or receive data, including audio or visual data as appropriate.

The ground station 31 can be in communication with the data network 26 or communication interface 40. The ground station 31 can have a processor and software and capabilities for uploading or downloading software or data to the aircraft. The ground station 31 might also capability to store, analyze, and manipulate flight data with data analysis or other statistical software. It should be recognized that the aircraft 10 might also have a computing system capable of storing, analyzing, and manipulating flight data with data analysis or other statistical software.

Figure 2:
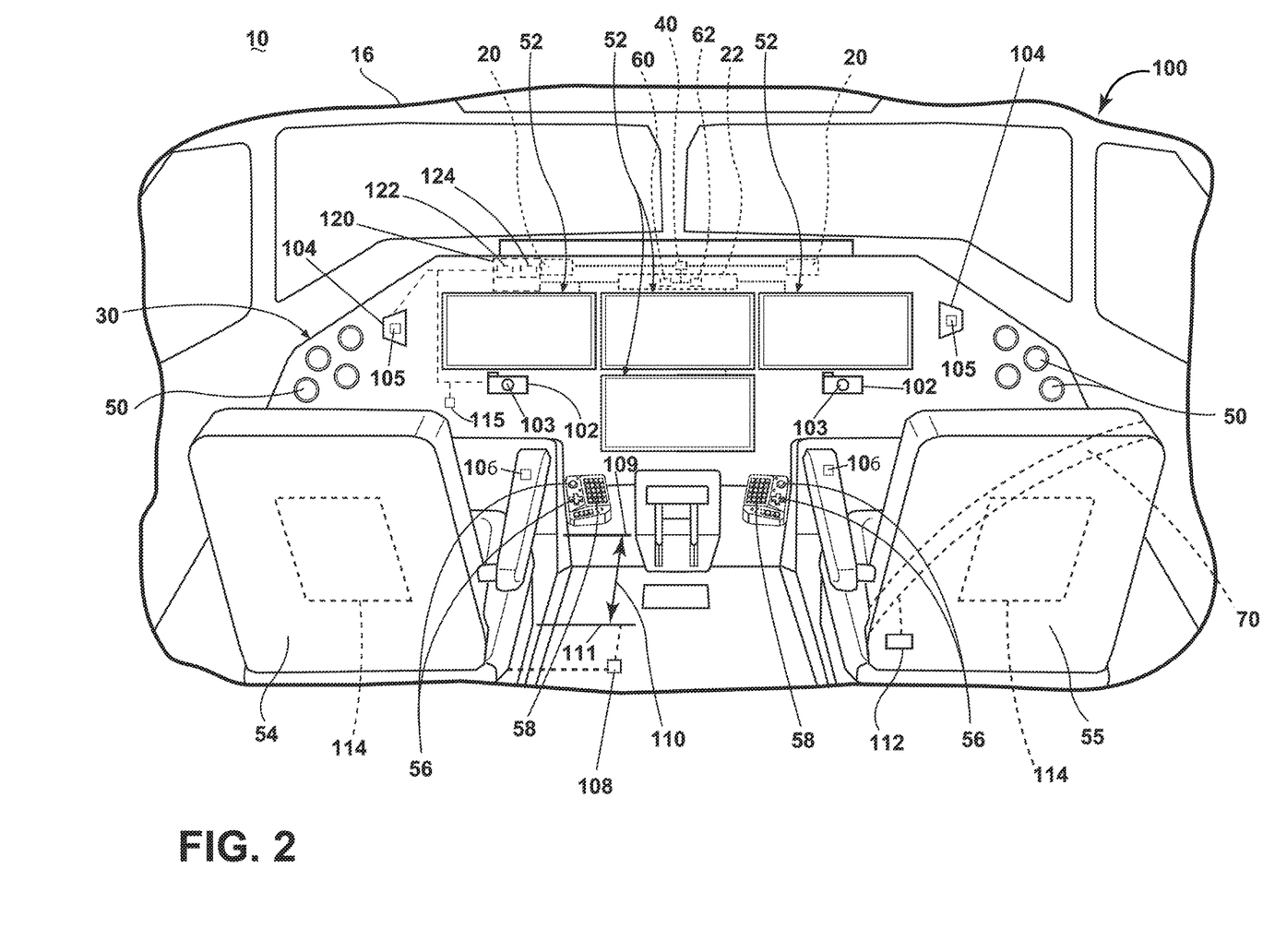
FIG. 2 is a perspective view of a cockpit of the aircraft of FIG. 1 including an attention tracking system according to various aspects described herein.

FIG. 2 illustrates a portion of the cockpit 16 of the aircraft 10 and an exemplary flight deck 30 having various instruments 50 and flight displays 52. A first pilot (herein, a "pilot") can be present in a seat 54 at the left side of the cockpit 16 and a second pilot (herein, a "co-pilot") can be present at the right side of the cockpit 16 in a seat 55 and the flight deck 30 can be located in front of the pilot and co-pilot and can provide the flight crew with information to aid in operating the aircraft 10. The flight displays 52 can include either primary flight displays or multi-function displays and can display a wide range of aircraft, flight, navigation, and other information used in the operation and control of the aircraft 10. Further, both the various instruments 50 and flight displays 52 of the flight deck 30 can provide one or more visual indicia indicative of a corresponding health condition of one or more of the aircraft systems 20.

The instruments 50 and flight displays 52 can be laid out in any manner including having fewer or more instruments or displays. Further, the flight displays 52 need not be coplanar and need not be the same size. A touch screen display or touch screen surface can be included in the flight display 52 and may be used by one or more flight crew members, including the pilot and co-pilot, to interact with the systems of the aircraft 10. Such touch screen surface can take any suitable form including that of a liquid crystal display (LCD) and can use various physical or electrical attributes to sense inputs from the flight crew. It is contemplated that the flight display 52 can be dynamic and that one or more cursor control devices 56 and/or one or more multifunction keyboards 58 can be included in the cockpit 16 and can be used by one or more flight crew members to interact with the systems of the aircraft 10. In this manner, the flight deck 30 can be considered a user interface for the aircraft systems 20 and the aircraft 10.

The flight control computer 22 can be operably coupled to components of the aircraft 10 including the aircraft systems 20, instruments 50, flight displays 52, touch screen surfaces, cursor control devices 56, keyboards 58, etc. The flight control computer 22 can receive inputs from any number of aircraft systems 20 or software programs responsible for managing the acquisition and storage of data. The flight control computer 22 can also be in the form of a controller, and can be connected with other controllers of the aircraft 10. The flight control computer 22 can include memory 60 and processing units 62, which can be running any suitable programs to implement a graphical user interface (GUI) and operating system. The flight control computer 22 can include or be associated with, any suitable number of individual microprocessors, power supplies, storage devices, interface cards, auto flight systems, flight management computers, and other standard components. The flight control computer 22 can include or cooperate with any number of software programs (e.g., flight management programs) or instructions designed to carry out the various methods, process tasks, calculations, and control/display functions necessary for operation of the aircraft 10.

The communication interface 40 can be communicably coupled to the flight control computer 22 or other processors of the aircraft 10 as well as any number of the plurality of aircraft systems 20 to transfer information on and off the aircraft 10. The communication interface 40 can include any desired communication mechanism capable of wirelessly linking with other systems and devices, such as by radio contact in a non-limiting example. For example, one of the aircraft systems 20 can be in the form of a distress tracker 21 configured to transmit a state of aircraft distress (for example, "normal," "abnormal," or "distressed").

A pilot tracking system or tracking system 100 is illustrated as being in communication with the flight control computer 22. It will be understood that the tracking system 100 can be hard wired to the flight control computer 22 or can communicate in any suitable manner with the flight control computer 22 including via wireless communication. Alternatively, the tracking system 100 can be included as a module within the flight control computer 22.

The tracking system 100 can include at least one imaging module 102 and at least one audio module 104. The imaging module 102 can include an image sensor 103 configured to sense visual information about a pilot or co-pilot, such as rapid eye movement, eyes moving one direction or another, being open or closed, a direction of gaze, or a facial state such as eyebrows raised or lowered, by way of non-limiting examples and provide an output signal based thereon. An eye movement or body movement parameter can be stored by the tracking system 100 The imaging module 102 or the flight control computer 22 can also be in signal communication with any of the flight displays 52, such as to display a visual indication based on the sensed visual information from the imaging module 102.

The audio module 104 can include an audio sensor 105 configured to sense audio information about a pilot or co-pilot, such as a language being spoken in the cockpit 16, a voice volume, slurred or altered speech, a speech pattern, or sounds that can occur due to pilot or co-pilot interaction with an aircraft system 20 such as striking the flight deck 30 or typing on the multifunction keyboard 58 and provide an output signal based thereon. The audio module 104 can also provide audio feedback or sound to the pilot or co-pilot, such as through speakers mounted within the cockpit or through headphones worn by the pilot or co-pilot. Further, the audio module 104 can be in signal communication with the imaging module 102. For example, the imaging module 102 can provide an indication for transmission through the audio module 104, such as spoken commands in a low-visibility environment within the cockpit 16. The audio module 104 can also provide a signal for transmission via the imaging module 102, such as a flashing light display or text-based indicator to be read by a pilot or co-pilot.

At least one biometric sensor 106 configured to sense a biometric parameter of the pilot or co-pilot can be included in the tracking system 100. For example, a biometric sensor 106 positioned on the first seat 54 can be configured to sense or detect a heart rate, breathing rate, perspiration rate, or bodily motion of the pilot when the pilot is sitting in the first seat 54. Alternatively, the biometric sensor 106 can be positioned on a wearable device such as a wrist strap or headband. In still another example, the biometric sensor 106 can be in the form of an optical sensor, e.g. a camera that monitors the pilot or co-pilot.

In addition, a seat tracking module 108 can control a seat distance 110 between the first seat 54 and the flight deck 30. While not shown, the second seat 55 can also include such a seat tracking module 108. Further, a seat belt sensor 112 can sense the position of a seat belt 70 on the first seat 54 or the second seat 55, such as the seat belt 70 being buckled or unbuckled.

A haptic feedback generator 114 can be coupled or integrated with either or both of the first and second seats 54, 55. The haptic feedback generator 114 can be configured to vibrate, such as a steady or varying vibration pattern, to provide feedback to the pilot or co-pilot. In a non-limiting example wherein the aircraft 10 is not level during flight in low-visibility conditions, the haptic feedback generator 114 can vibrate on a right-hand portion or left-hand portion of the seat 54, 55 to indicate to a pilot or co-pilot which direction to bank the aircraft 10 for correct orientation when flying.

A timer 115 can also be included in the tracking system 100 and is illustrated as being coupled to the flight deck 30. The timer 115 can be positioned anywhere within or outside of the cockpit 16. The timer 115 can be configured to track an elapsed time of an event or to provide an alarm or other indication at a predetermined time. Non-limiting examples where the timer 115 can be utilized include tracking an elapsed time of flight, an elapsed time of a pilot interaction with an aircraft system 20 (such as updating flight records via the multifunction keyboard 58), tracking an elapsed sleep time, indicating a time for changing a flight direction, or indicating a wake time.

An additional controller 120 having a processor 122 and a memory 124 can also be included in the tracking system 100. The controller 120 is illustrated as being coupled to the flight deck 30 and in signal communication with any or all of the flight control computer 22, instruments 50, flight displays 52, memory 60, processing unit 62, imaging module 102, audio module 104, biometric sensor 106, seat tracking module 108, seat belt sensor 112, haptic feedback generator 114, or timer 115. Dashed lines have been used to illustrate a portion of the signal connection between the above-described components. The lack of a dashed line for signal connections is done for clarity of the figures, and it will be understood that components not connected by a dashed line can nonetheless be in signal communication.

Figure 3:
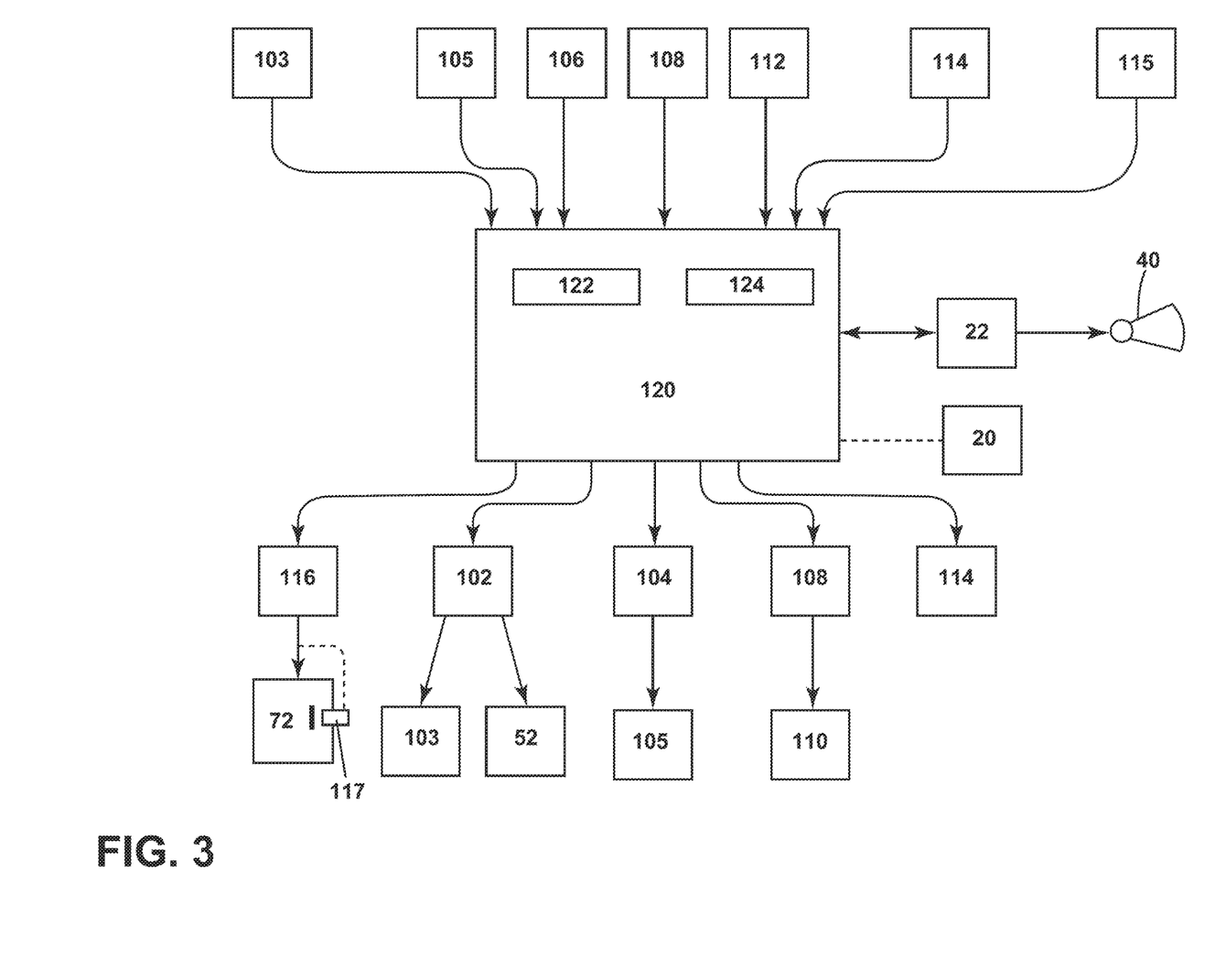
FIG. 3 is a schematic illustration of the attention tracking system of FIG. 2 according to various aspects described herein.

FIG. 3 schematically illustrates components of the tracking system 100 in exemplary communicative connection, where a separate controller 120 is shown in signal connection with the various modules and sensors described above. Alternatively, it will be understood that the flight control computer 22 can be utilized or that each module or any combination of modules can include their own controller, processor, or memory. Arrows have been included to indicate an exemplary signal or control direction, and are provided for clarity in discussion. It will be understood that any signal communication or control between connected components in FIG. 3 can be transmitted in either direction, and an arrow's illustrated direction does not imply a one-way signal or control direction.

A door lock module 116 with a door lock sensor 117 can further be included in the tracking system 100. For example, a cockpit door 72 can include the door lock module 116 configured to sense whether the door 72 is locked or unlock. The module 116 can also automatically lock or unlock the door 72 based on a control signal within the tracking system 100.

The controller 120 can be operably connected to and receive input from any or all of the flight control computer 22, image sensor 103, audio sensor 105, biometric sensor 106, seat tracking module 108, seat belt sensor 112, haptic feedback generator 114, timer 115, or door lock module 116. Any of the inputs received by the controller 120 can be stored in the memory 124. For example, the memory 124 can store a history of audio input or recordings from data gathered within the cockpit 16, or an elapsed time since a pilot last interacted with a flight display 52 (FIG. 2).

The processor 122 of the controller 120 can send a signal or control command to any or all of the imaging module 102, audio module 104, seat tracking module 108, haptic feedback generator 114, or door lock module 116. In another non-limiting example, the processor 122 can send a signal to the imaging module 102, such as a visual message to be read by the pilot or co-pilot on the flight display 52, or a command to enable or disable the image sensor 103.

It is further contemplated that the controller 120 of the tracking system 100 can issue a signal or command to another aircraft system, such as the communication interface 40 via the flight control computer 22. In such a case, the controller 120 can communicate with an external aircraft or ground station (not shown). The controller 120 can also be communicatively coupled with any other aircraft system 20 as desired.

Figure 4:
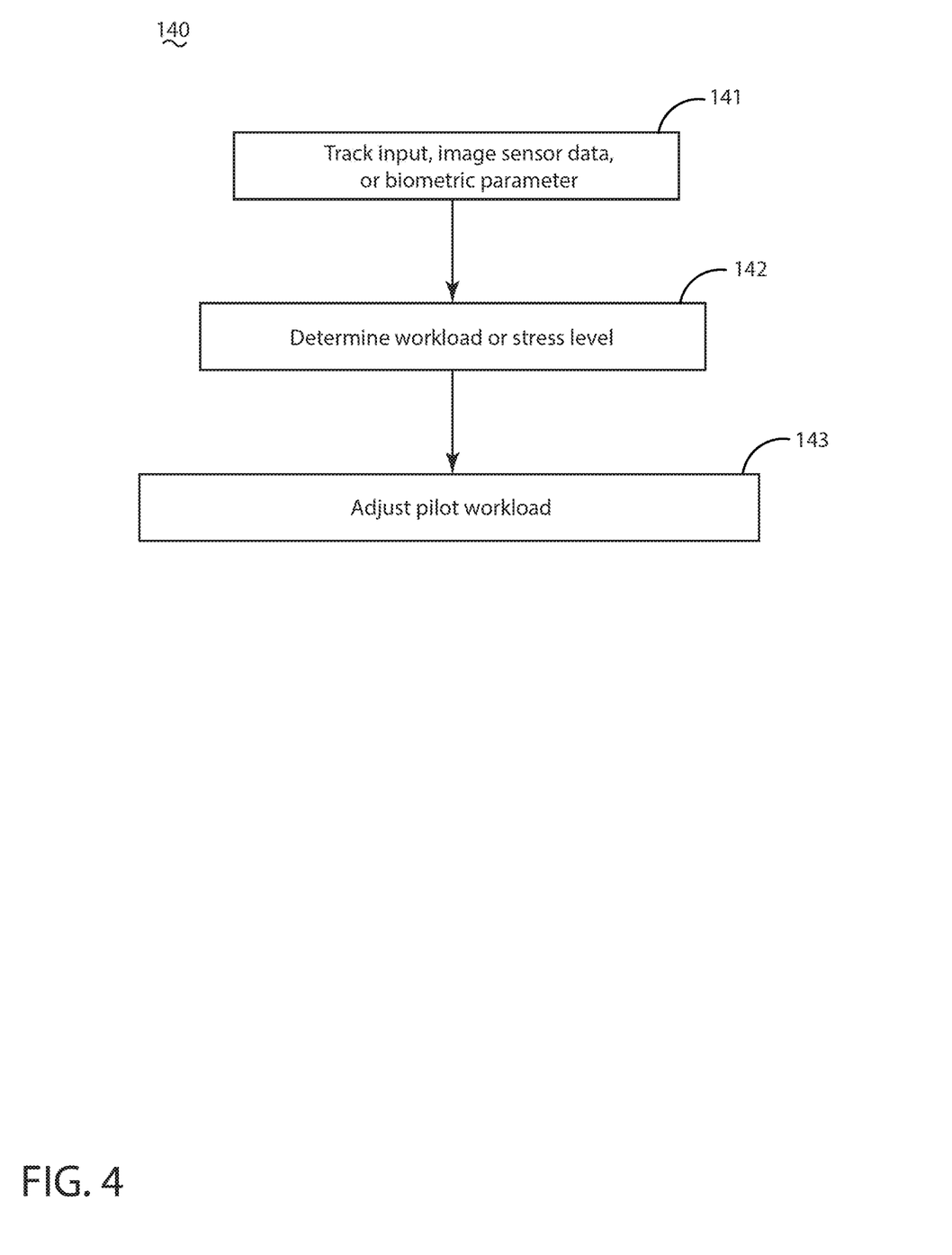
FIG. 4 is a flowchart illustrating a method of adjusting pilot workload during a flight of an aircraft of FIG. 1 according to various aspects described herein.

Referring now to FIG. 4, a method 140 of adjusting pilot workflow during a flight is illustrated. The method 140 begins at 141 with tracking inputs by a pilot or tracking image sensor 103 data or a biometric parameters of the pilot to determine a stress level of the pilot during flight of the aircraft 10 by using at least one sensor within the tracking system 100. The tracking of inputs, sensor data or biometric parameters can occur over distinct periods of time such as over an entire flight, or portions of a flight such as an elapsed time over a geographic location, an elapsed time a pilot has been on-board, or an elapsed time of a flight phase such as flight take off, flight landing or cruising.

Tracking inputs by the pilot can be an indication of the pilot's workload. For example, tracking pilot input can be accomplished via the image sensor 103, such as visually detecting the pilot's hand interacting with the keyboard 58 or flight display 52. In an example where the flight display 52 includes a touchscreen, the controller 120 can detect that the pilot has touched or interacted with the touchscreen flight display 52. Tracking pilot input can also be accomplished via the flight control computer 22 which is communicatively coupled to the controller 120, including tracking that the pilot has interacted with or entered input to any cockpit system e.g. the keyboard 58 or the cursor control device 56.

Tracking a pilot's stress level can be accomplished by tracking a pilot's eye movements or body movements from the image sensor 103 or by tracking various biometric parameters of the pilot. For example, the image sensor 103 can track both the eye movements and body movements of the pilot during all or portions of the flight. In addition, biometric parameters of the pilot such as heart rate, breathing rate, skin temperature, and the like, can be indicative of the pilot's stress level. It should be recognized that this data can be used to make real-time decisions about pilot workload or stress level during a flight or the data can be saved to a database and processed after the flight.

At 142, the controller 120 can determine the workload or stress level of the pilot based on the tracked pilot input, image sensor 103 data, or biometric parameter(s) from 141. For example, the timer 115 in conjunction with the flight control computer 22 can indicate to the controller 120 that the pilot has input multiple inputs into various avionics systems over a short period of time and is backed up on flight control computer 22 requests. The controller 120 can then determine the rate at which the pilot is addressing flight control computer 22 requests and determine the workload level of the pilot.

The controller 120 can also or alternatively determine, at 142, a stress level of the pilot based image sensor 103 data. For example, if the pilot's eyes are rapidly moving from screen to screen the controller 120 can determine the pilot stress level by correlating the movements with other real-time parameters, against pre-existing data, or above a pre-determined threshold level.

Similarly, the controller 120 can also or alternatively determine, at 142, a stress level of the pilot based on the biometric parameter. For example, the biometric sensor 106 can determine a pilot's rate of breathing, heart rate, pulse rate, and the like. The controller 120 can determine the pilot stress level by correlating any of the biometrics parameters with other real-time parameters such as data from the image sensor 103, against pre-existing data, or above a predetermined threshold level.

At 143, the controller 120 can adjust the pilot workload during flight when one of the pilot workload or pilot stress level exceeds a predetermined threshold. For example, if the controller 120 determines that the pilot's stress level is above a predetermined threshold value based on sensor readings from one of the image sensor 103 or biometric sensor 106 then the controller 120 can be programmed to shift certain tasks such as non-critical or non-essential pilot tasks to the co-pilot or other crew member. In addition or alternatively, the controller 120 can be programmed to shift the non-critical or non-essential pilot tasks to a future time frame when the pilot has less tasks in his workload.

Figure 5:
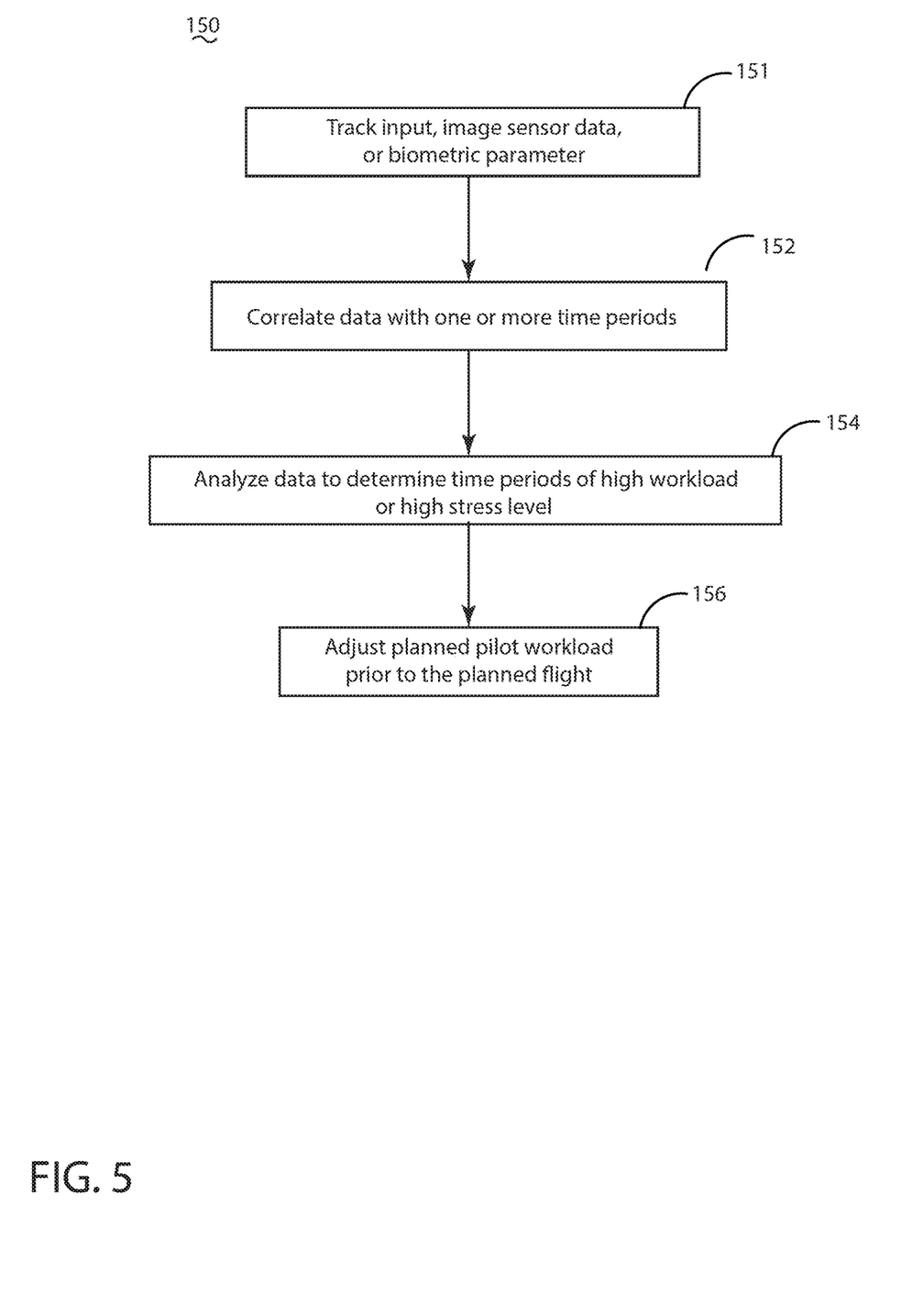
FIG. 5 is a flowchart illustrating another method of adjusting a planned pilot workload for an aircraft of FIG. 1 before the planned flight according to various aspects described herein.

Turning to FIG. 5, a method 150 of adjusting a planned pilot workload before the planned flight is shown. The method includes, at 151, tracking inputs by a pilot, or tracking image sensor 103 data, or a biometric parameter of the pilot during flight of the aircraft 10 during one or more aircraft flights. Since flights often take place over the same flight path, such as from city-to-city, flight data can be collected that is representative of a typical flight between the two cities. At this step, it is contemplated that data can be tracked and collected from multiple flights over various time frames and preferably from flights that fly the same or similar flight paths. The data can be tracked, collected, and analyzed to understand time frames during a flight that pilot's experience heavy workloads and high stress. The data processing can be done on or off aircraft 10, where the flight control computer 22 or other processors on the aircraft 10 can adjust the expected pilot workload before the planned flight.

At 152, data from the image sensor 103, biometric sensor 106 (i.e. biometric parameters), and pilot inputs responsive to the flight control computer 22 can be correlated with one or more time periods of the flight. In other words, at this step 152, for any given flight, data representing a pilot's workload or stress level can be collected and correlated over distinct periods of time such as over an entire flight, or portions of a flight such as an elapsed time over a geographic location, an elapsed time a pilot has been on-board, or an elapsed time of a flight phase such as flight take off, flight landing or cruising. In this example, the timer 115 can track the time of flight which can be correlated with the collected pilot data across the all or a portion of the flight. Data from each recorded flight can be stored onboard or can be transmitted offsite to a ground station 31 for analysis and processing.

At 154, analysis of the data, either on-aircraft by an on-board processor or off-site by the ground station, can identify which of the time periods the pilot's workload was above a predetermined threshold value indicative of a pilot experiencing high workload volumes or high stress levels. In one example, data from multiple independent flights with similar flight paths can be analyzed to understand specific time frames the pilots of each of flights experienced high workload volumes or stress levels. Using this data, the controller 120 or other processor can predict when a pilot on a planned flight will likely experience increases in workload or higher stress levels.

At 156, prior to a planned flight, the controller 120 or other processer that is operatively connected to the flight control computer can adjust the expected pilot work load during the planned flight. In this scenario, the controller 120 or other processer can predict heavy workload periods in the planned flight and can adjust the pilot workload by shifting tasks from the predicted heavy workload period to periods where the pilot workload if predicted to be light. Moreover, the controller 120 or other process can predict when work load will be heavy for the entire crew and can predict when additional or less crew may be required for certain flights or certain conditions.

To the extent not already described, the different features and structures of the various embodiments can be used in combination, or in substitution with each other as desired. That one feature is not illustrated in all of the embodiments is not meant to be construed that it cannot be so illustrated, but is done for brevity of description. Thus, the various features of the different embodiments can be mixed and matched as desired to form new embodiments, whether or not the new embodiments are expressly described. All combinations or permutations of features described herein are covered by this disclosure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of adjusting a planned pilot workload before a planned flight, the method comprising:
    tracking over a time period, using at least one sensor, inputs by a pilot into an avionic system responsive to a request from a flight control computer during one or more flights of an aircraft prior to the planned flight;
    determining a rate at which the inputs by the pilot are made;
    determining the pilot workload based upon the rate;
    correlating, using a controller that is operatively connected to the at least one sensor, the pilot workload with one or more time periods for analysis;
    identifying, using a processor that is operatively connected to a controller, which of the one or more time periods comprise pilot workload above a threshold value based on the analysis; and
    adjusting, using a controller that is operatively connected to a flight control computer, the pilot workload for the time periods above the threshold value of pre-planned pilot workload of the planned flight.

2. The method of claim 1 wherein the time period comprises one of elapsed time over a geographic location, an elapsed time a pilot has been on-board, or an elapsed time of a flight phase.

3. The method of claim 2 wherein flight phase comprises one of flight take off, flight landing, or cruising.

4. The method of claim 1 wherein the identifying which of the one or more time periods comprises pilot workload above a threshold value comprises comparing inputs by a pilot over a time period against a predetermined threshold.

5. The method of claim 4 wherein the identifying which of the one or more time periods comprise pilot workload above a threshold value occurs after a flight has ended.

6. The method of claim 1 wherein the adjusting the pilot workload comprises moving one or more pilot tasks by the controller to a different time period.

7. The method of claim 1 wherein the step of adjusting the pilot workload comprises adjusting crew roster for accommodating pilot workload.

8. The method of claim 1, further comprising: predicting, for the planned flight, at least one period for pilot workload above the threshold value based on the identifying.

9. The method of claim 1, wherein the at least one sensor is an image sensor arranged to detect an interaction of a pilot's hand interacting with a keyboard.

10. The method of claim 1, wherein the at least one sensor includes a flight control computer arranged to track the inputs by the pilot to a cockpit system.

\* \* \* \* \*

UNITED STATES PATENT AND TRADEMARK OFFICE
CERTIFICATE OF CORRECTION

| | | |
|---|---|---|
| PATENT NO. | : 11,928,970 B2 | Page 1 of 1 |
| APPLICATION NO. | : 16/709409 | |
| DATED | : March 12, 2024 | |
| INVENTOR(S) | : Schwindt | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 836 days.

Signed and Sealed this
Twenty-second Day of October, 2024

*Katherine Kelly Vidal*

Katherine Kelly Vidal
*Director of the United States Patent and Trademark Office*